(12) United States Patent
Mehta et al.

(10) Patent No.: US 11,312,729 B1
(45) Date of Patent: Apr. 26, 2022

(54) CONTINUOUS MANUFACTURE OF DBX-1

(71) Applicant: U.S. Government as Represented by the Secretary of the Army, Dover, NJ (US)

(72) Inventors: Neha Mehta, Succasunna, NJ (US); Jon G. Bragg, Centerbrook, CT (US); Matthew L. Jorgensen, Centerbrook, CT (US); Andrew G. Pearsall, Centerbrook, CT (US); Jerry S. Salan, Centerbrook, CT (US); Daniel W. Ward, Centerbrook, CT (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 272 days.

(21) Appl. No.: 16/655,446

(22) Filed: Oct. 17, 2019

(51) Int. Cl.
  *C07F 1/08* (2006.01)
  *B01J 19/24* (2006.01)
  *C06B 41/00* (2006.01)

(52) U.S. Cl.
  CPC ............... *C07F 1/08* (2013.01); *B01J 19/242* (2013.01); *C06B 41/00* (2013.01); *B01J 2219/00033* (2013.01); *B01J 2219/00081* (2013.01)

(58) Field of Classification Search
  CPC ............. C07F 1/08; C07F 1/06; C07D 257/06
  USPC .................................................. 548/101, 251
  See application file for complete search history.

(56) References Cited

U.S. PATENT DOCUMENTS

| 7,833,330 B2 | 11/2010 | Fronabarger |
| 8,071,784 B2 | 12/2011 | Fronabarger |
| 8,163,786 B2 | 4/2012 | Fronabarger |
| 9,278,984 B2 | 3/2016 | Klapotke |

OTHER PUBLICATIONS

Fronabarger, et al., "DBX-1 A Lead Free Replacement for Lead Azide", Propellants, Explosives, Pyrotechnics, vol. 36, p. 541-550, 2011.

*Primary Examiner* — Charanjit Aulakh
(74) *Attorney, Agent, or Firm* — John P. DiScala

(57) ABSTRACT

The present invention is directed to a process for continuous production of copper (I) nitrotetrazolate (DBX-1) by reacting aqueous copper salt with aqueous 5-nitrotetrazolate salt in the presence of a reducing agent. All the reactants are introduced into a continuous flow reactor system, which is composed of a temperature controlled tubular reactor and a mixer that allows for radial mixing. An optional stirred tank reactor may also be incorporated into the process to complete the reaction and allow for crystal growth.

14 Claims, 3 Drawing Sheets

CONTINUOUS MANUFACTURE OF DBX-1

RIGHTS OF THE GOVERNMENT

The inventions described herein may be manufactured and used by or for the United States Government for government purposes without payment of any royalties.

FIELD OF INVENTION

The invention disclosed herein relates generally to methods for manufacturing the explosive DBX-1 and more specifically to continuous manufacturer of the DBX-1 explosive in a continuous flow reactor system.

BACKGROUND OF THE INVENTION

Primary explosives are commonplace for the initiation of an explosive chain reaction in military and commercial blasting. The high sensitivity to external impetus and production of a short but powerful shockwave allows small quantities of primary explosive material to initiate significantly larger quantities of insensitive secondary explosive material. This has the positive effect of minimizing the overall sensitivity of an explosive system. Two of the most widely used secondary explosives are lead(II) azide (LA) and lead(II) styphnate—which have come under severe scrutiny due to the toxicity that the use of lead affords. The use of lead based primary explosives has resulted in significantly contaminated air and soil in military training grounds and at government and commercial firing ranges, posing a substantial toxicity hazard to the personnel tasked with working in these surroundings. Furthermore, azide anions are known to form extremely sensitive explosive complexes if exposed to a moisture-rich environment, whereby azide reacts with carbon dioxide to form hydrazoic acid, a toxic and explosive material. Other hazardous complexes are formed when azide complexes with metals also found within an energetic system. For example, in aging munitions, which contain an azide and a copper detonator shell, the unintended formation of copper azides has led to fatal accidents as bomb investigators and explosive ordinance disposal teams have attempted to move such items.

Thus, a need exists for a more environmentally friendly, less toxic replacement for the primary explosive lead azide. One promising candidate as a direct replacement is copper(I) nitrotetrazolate (DBX-1). DBX-1 has comparable properties to LA as an explosive; but does not have the toxicity or other drawbacks that LA suffers from. In spite of this, DBX-1 has made little progress in replacing LA due to issues with its production.

The synthesis of DBX-1 was first disclosed in a paper by John W. Fronabarger et al., "DBX-1 A Lead Free Replacement for Lead Azide", published in Propellants, Explosives, Pyrotechnics, Vol. 36, p. 541-550, 2011. The process is also described in the following patents: U.S. Pat. Nos. 7,833,330; 8,071,784; 8,163,786; and 9,278,984. The chemistry of the reaction is well detailed within these publications, such that the disclosure made herein is to make the synthesis procedure amendable to continuous manufacture. As such, the information and process described in the above referenced patents are incorporated herein their entirety.

To the best of our knowledge, all described synthetic procedures towards DBX-1 to date have used batch manufacture, and this disclosure will provide a method for continuous manufacture of DBX-1. The continuous manufacturer of DBX-1, a highly sensitive primary explosive, presents numerous advantages over conventional batch manufacture methods. Continuous technology offers a more compact equipment footprint compared to an equivalent scale batch manufacturing process. This does not only mean that less space needs to be afforded to store the reactor, but through continuous generation of DBX-1, less primary explosive is accumulated within the reactor at any one time, dramatically improving the overall safety of the process and reducing the associated effect of an unintended initiation.

Typically, and in the prior art described above, DBX-1 is prepared from sodium 5-nitrotetrazolate (NaNT), a compound that has been used as a precursor to other explosives which are produced on a large scale. The synthesis of DBX-1 is shown in scheme 1 with preferred reagents, comprises of the reaction of a copper salt with a 5-nitrotetrazolate salt in the presence of a reducing agent.

Scheme 1: Prior art synthesis of DBX-1 using sodium 5-nitrotetrazolate (NaNT), copper chloride ($CuCl_2$) as the copper source and sodium ascorbate (NaAsc) as the reducing agent.

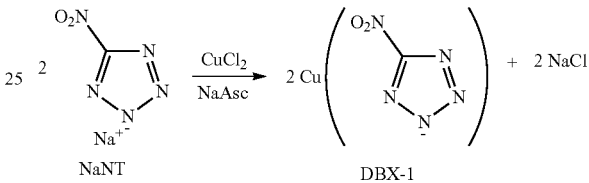

Further in the typical prior art method detailed above, there is a common observation of an 'induction period' whereby the reaction progresses via a problemic reactive and highly sensitive explosive intermediates. This induction period has been described to be unpredictable and variable in an unseeded reaction, and it has been well observed that the reaction may stall at an unproductive intermediate and not proceed to the desired DBX-1.

Thus a need exists for a more robust synthesis of DBX-1 that is preferably more streamlined than existing batch techniques, and can be scaled without any additional issues.

SUMMARY OF THE INVENTION

It is an objective of the present invention to provide a method for continuous production of copper(I) nitrotetrazolate (DBX-1).

In one aspect of the invention, reactants such as aqueous copper salt and aqueous 5-nitrotetrazolate salt are mixed and introduced into a continuous flow reactor system, and a reducing agent is thereafter added to the mixture. The continuous flow reactor system is comprised of a tubular reactor and a mixer which imparts energy to radially mix the reactants within the tubular reactor to form a slurry containing DBX-1. The contents of the tubular reactor may be further introduced into a stirred tank reactor to allow for reaction completion. Thereafter, the reactants are filtered and washed.

In another aspect of the invention, the reactants inside the tubular reactor may be introduced into a single continuous stirred tank reactor (CSTR) or more than one CSTR setup in series.

BRIEF DESCRIPTION OF THE DRAWINGS

Further features and advantages of the present invention may be understood from the drawings.

DETAILED DESCRIPTION

Disclosed herein is a method for continuous production of copper (I) nitrotetrazolate (DBX-1) by: a) reacting copper salt with 5-nitrotetrazolate salt in the presence of a reducing agent; b) combining the reagents within a temperature controlled tubular reactor and 3) mixing the reagents using a secondary mixer imparted onto the tubular reactor. An optional stirred tank reactor may also be incorporated into the process to complete the reaction and allow for crystal growth.

The invention disclosed may be embodied in many ways, including slight variation in starting materials, different orders of reacting such materials, variation of process conditions, modifications of equipment and equipment setup. This invention is not restricted to such factors, but rather outline the novel continuous synthesis of DBX-1.

Preferred reactant components are aqueous copper (II) chloride, the aqueous sodium 5-nitrotetrazolate, and the reducing agent is most preferably aqueous sodium ascorbate.

In this invention, a continuous flow reactor system is used to efficiently mix the reactants and convey the resultant solid slurry to a filtration system where the product is continuously washed and isolated. An example description of the process is presented herein, not as a definitive method, but as a process framework, which can be modified according to the description enclosed within this document.

Figure 1:
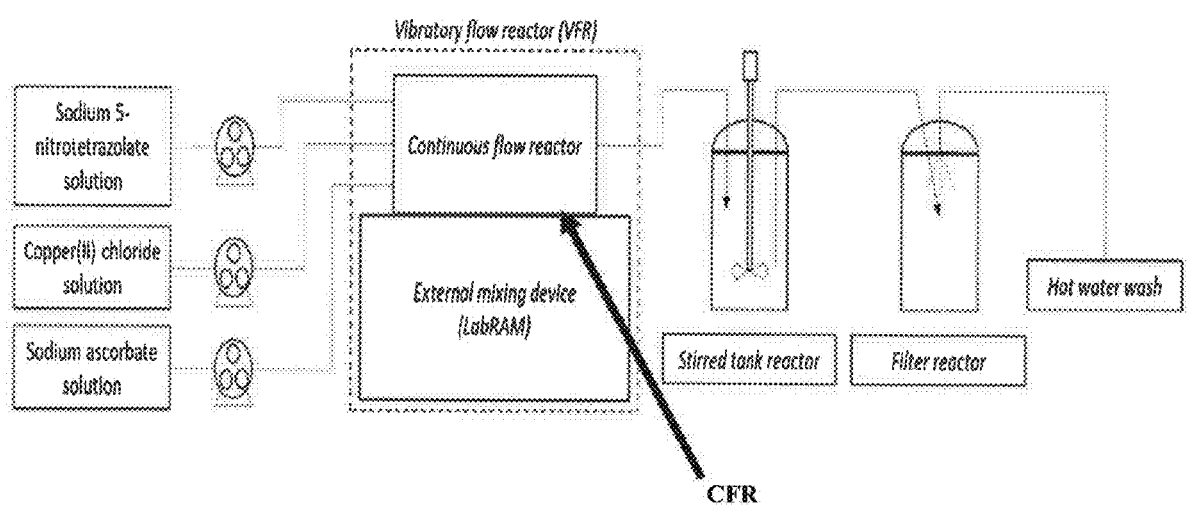
FIG. 1 is a schematic representation of the equipment setup for the continuous synthesis of DBX-1.

FIG. 1 is an illustration of the equipment setup for preparing DBX-1 using the methods described herein. Individual pumps are used to transport the reactant streams from separate storage tanks or vessels into the continuous flow reactor system. The continuous flow reactor system consists of a tubular reactor such as a jacketed tubular reactor also referred to as a plug-flow reactor (PFR) and a mixing device.

Figure 2:
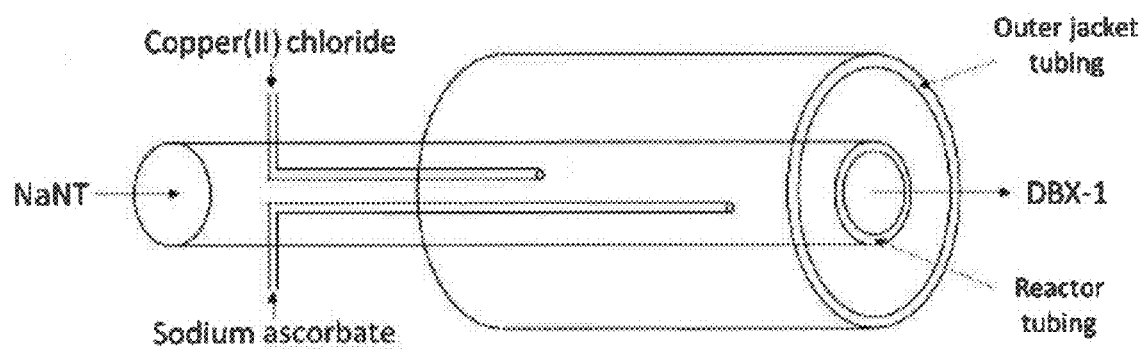
FIG. 2 is a schematic of the tubular reactor setup for the introduction of the reactant components.
Figure 3:
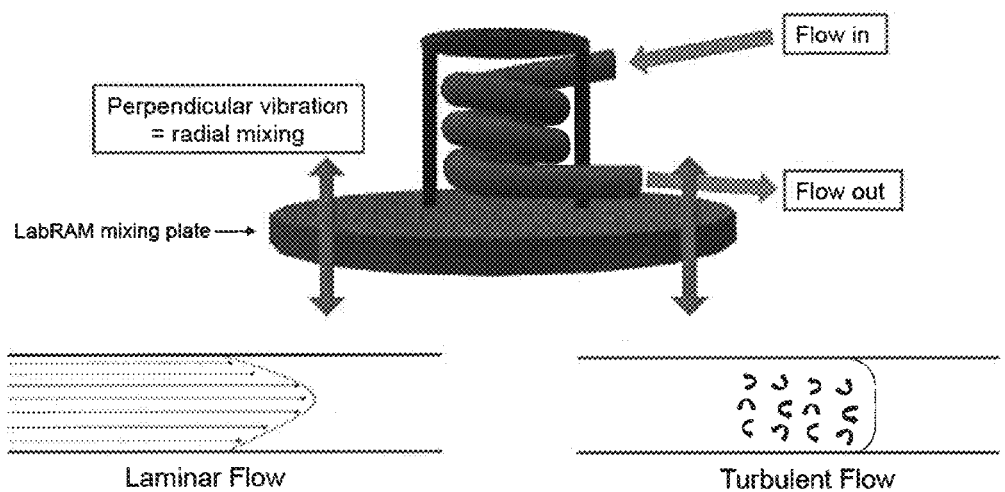
FIG. 3 is an illustration of a preferred type of mixing for the tubular reactor.

A PFR is a type of reactor where fluid moving through the reactor travels as discrete 'plugs', with each plug being mixed radially and having different composition due to the age-time of the plug. The ideal PFR has no axial dispersion or mixing along the length of the reactor. This allows for chemical reactions to produce products as discrete segments within the tube. An exemplary PFR is illustrated in FIG. 2, which consists of an internal tube surrounded by an external tube of greater diameter. The reactants are introduced and contained within the internal tubing. The outer external tube, surrounding the internal tube, contain heat transfer fluid to regulate and/or maintain the temperature of the contents in the inner tube.

FIG. 2 illustrates an exemplary process by first pumping an aqueous solution of 5-nitrotetrazolate through a heat exchanger to pre-heat this stream before entering the PFR inner tube. Downstream from where 5-nitrotetrazolate is introduced, an aqueous solution of copper (II) chloride is pumped into the PFR internal tubing, followed by an aqueous solution of sodium ascorbate, which is pumped into the internal tubing further along the PFR. This allows for mixing of the sodium 5-nitrotetrazolate and copper (II) chloride solutions prior to introduction of the sodium ascorbate.

The PFR is situated on top of a resonant acoustic mixer (RAM). One exemplary RAM is the Resodyn Resonant Acoustic Mixer (LabRAM) which is a non-contact mixing device primarily used for efficient mixing within a closed vessel. The LabRAM uses low frequency (60 Hz) acoustic energy, which is translated to vibrational energy of the mixing plate. The vibrations are then translated throughout the PFR mounted to the mixing plate. The entire system vibrates in resonance, providing efficient energy transfer to materials within the PFR with essentially no loss of the systems mechanical energy. The energy input is tunable from low energy up to an acceleration of 100 G. Intense mixing is generated in the form of microscale eddies which efficiently mix the contents inside the PGR inner tube.

In one embodiment, a standalone RAM is mounted directly under the PFR to provide rapid and efficient mixing of the reactants in the PFR. The mixer serves to provide an area of turbulent mixing, enhancing the otherwise inefficient laminar flow that is present within the PFR. As a result, the contents of the PFR are well mixed along the length of the inner tubing in a radial manner, which has particular importance for the mixing zones where copper (II) chloride and sodium ascorbate solutions are dosed into the reactor tubing. Furthermore, the enhanced mixing afforded by the standalone RAM improves conveyance of solids along the PFR, which is important for conveying the reaction product (i.e. slurry containing DBX-1).

After combination of the reactants in the PFR, followed by residence time within the PFR, the contents (slurry containing DBX-1 product) can be washed, filtered and the DBX-1 isolated. Alternatively, the PFR contents can flowed directly into a stirred tank reactor, a continuous stirred tank reactor (CSTR) or multiple CSTRs set up in series. For example, a PFR flowing into a single CSTR or into multiple CSTRs operating either in series or in parallel. The contents of the CSTR are held at a similar temperature to the PFR and well mixed using overhead stirring. The CSTR may provide additional residence time for the reaction to complete and crystal growth to occur. Once the desired residence time has elapsed, or the CSTR contents have reached the desired fill volume, a desired volume of the reaction mixture is siphoned from the CSTR using a vacuum transfer method. A dip tube is set at a desired height in the CSTR such that only a limited volume of the CSTR contents are vacuum transferred from the CSTR. The vacuum transfer tubing from the CSTR is set in series to a spray wash the DBX-1 product with hot water immediately after transferring out of the CSTR. The washed DBX-1 is then filtered under suction. It should be noted that the temperature of the entire process from introduction of the reactions to isolation of the finished DBX-1 product should be monitored and maintained at an elevated temperature of about 75° C. to about 95° C.

Example 1

A continuous flow system was engineered by mounting a tubular reactor (or PFR) on top of an acoustic mixer. The reactor coil was engineered using ¼" outer diameter (OD) Teflon PTFE tubing. A temperature jacket was engineered using ½" OD and ⅜" inner diameter (ID) Teflon PTFE tubing. The dosing lines were selected to be 1/16" OD in order to fit within the reactor tubing. The tubing were engineered into a coil shape and mounted to a resonant acoustic mixer (LabRAM II™ available from Resodyn). A stirred tank reactor (STR) was set up using a Mettler Toledo Optimax™ reactor equipped with a 1 L glass reactor fitted with a half-moon impeller, internal temperature probe, and a Mettler Toledo particle vision and measurement (PVM) probe.

The jacket temperature of the tubular reactor and the internal reactor temperature of the STR were set to 85° C.

To meet the minimum stir volume and ensure the tip of the PVM probe was submerged, a heel of DBX-1 was generated in the STR (100 ml). Aqueous copper(II) chloride solution (1M, 13.14 ml) and DBX-1 seed crystals (6 wt %, 130 mg, 42 ml water) were charged to the tubular reactor. Aqueous NaNT (6 wt %, 42 ml) was slowly added such that the reactor contents remained above 80° C. Aqueous sodium ascorbate solution (1M, 3.68 ml) was dosed to the reactor at 0.15 ml/min. Once all reactants had been dosed to the reactor, the final NaNT concentration was 2.5 wt %. Upon completion of the sodium ascorbate dose, the reactor proceeded via a solid orange intermediate before the crystalline red product precipitated from solution. The total induction time from the end of the dose to precipitation of DBX-1 was 30 minutes.

The flow reactor was operated using peristaltic pumps and balances to dose the aqueous reactants, allowing accurate control of feed rates to create a total flow rate within the tubular reactor of 15 g/min (the same process has been repeated at 5 g/min). Aqueous NaNT solution was the first reagent to enter the continuous flow reactor at a flow rate of 8.36 g/min and was pre-heated to 80° C. using an AFR mixing plate. Aqueous copper(II) chloride (1M) was dosed into the tubular reactor at a flow rate of 3.32 g/min. After being allowed to mix, with the LabRAM set to an acceleration of 12 G, aqueous sodium ascorbate solution (1M) was dosed into the reactor tubing at 3.32 g/min. After experiencing residence time within the flow reactor, the flow reactor contents were entered the STR where an additional 6 minutes residence time was experienced. When the STR contents reached 500 ml, 100 ml of the reaction mixture was vacuum transferred to a filter reactor where the material was sprayed with excess hot deionized water at 80° C. and filtered under suction. The isolated solids were rinsed with 2-propanol and transferred to a conductive container for storage.

Powder X-ray diffraction of the dry product matched a simulated diffraction pattern generated from literature single crystal X-ray diffraction data using Mercury software provided by CCDC.29 Differential scanning calorimetry showed a Tonset=301.5 oC. (dec.) (5 oC./min, 0.419 mg). HR-TGA showed a weight loss of 55.4% (residual mass 44.6%), matching the theoretical weight loss assuming full conversion of DBX-1 to CuO of 44.79% (residual mass).

Example 2

An aqueous solution of sodium 5-nitrotetrazolate was fed into a temperature controlled tubular reactor at 12.44 g/min where it was mixed with feeds of aqueous copper(II) chloride and aqueous ascorbate at flow rates of 2.16 g/min and 0.39 g/min respectively. The mixture was allowed to react within the tubular reactor before entering a continuous stirred tank reactor (CSTR). The tubular reactor was mounted to an independent mixing device set to an acceleration of 12G, which provided constant turbulent mixing within the tubular reactor at all times. The temperature during the addition of reactants to the tubular reactor and during the CSTR phase was 95° C. The CSTR was allowed to fill to a total fill volume of 500 ml before an aliquot of 70 ml was transferred to the filter. The process of filling the CSTR to 500 ml and collecting 70 ml aliquots was repeated several times over, resulting in an average yield of 0.6 g (37%) DBX-1 isolated on the paper per aliquot.

The foregoing description of the preferred embodiment of the present invention has been presented for the purpose of illustration and description. It is not intended to be exhaustive or to limit the invention to the precise form disclosed. Many modifications and variations are possible in light of the above teachings. It is intended that the scope of the present invention not be limited by this detailed description but by the claims and any equivalents.

What is claimed is:

1. A process for continuous production of copper(I) nitrotetrazolate, DBX-1 comprising:
   a. introducing reactants, wherein the reactants comprises aqueous copper salt, aqueous 5-nitrotetrazolate salt, and a reducing agent into a continuous flow reactor system, and wherein the continuous flow reactor system comprises a tubular reactor and a mixer;
   b. imparting energy from the mixer to the reactants inside the tubular reactor to radially mix the reactants;
   c. forming a slurry containing DBX-1 inside the tubular reactor.

2. The process of claim 1, wherein the aqueous copper salt and aqueous 5-nitrotetrazolate are introduced into the tubular reactor and mixed before the reducing agent is introduced to the mixture.

3. The process of claim 1, wherein the tubular reactor is a plug flow reactor.

4. The process of claim 1, wherein the tubular reactor is temperature controlled.

5. The process of claim 1, wherein the slurry containing DBX-1 is introduced into at least one continuous stirred tank reactor (CSTR).

6. The process of claim 1, wherein the mixer is a resonant acoustic mixer.

7. The process of claim 1, wherein the reducing agent is sodium ascorbate in solution.

8. The process of claim 3, where the plug flow reactor comprises an inner tube and outer tube.

9. The process of claim 8, where the reactants are located in the inner tube of the plug flow reactor.

10. The process of claim 8, wherein the outer tube controls the temperature of the reactants in the inner tube.

11. The process of claim 5, further comprising collecting and filtering the DBX-1 reaction product from the CSTR.

12. A process for continuous production of copper(I) nitrotetrazolate, DBX-1 comprising:
   a. introducing mixing aqueous copper salt and aqueous 5-nitrotetrazolate salt into a tubular reactor, wherein the tubular reactor is comprised of an inner tube and outer tube;
   b. adding a reducing agent to the mixture to form a slurry comprising DBX-1;
   c. radially mixing the contents of the tubular reactor using an acoustic mixer;
   d. transferring the slurry into at least one stirred tank reactor.

13. The process of claim 12, wherein the stirred tank reactor is a continuous stirred tank reactor.

14. The process of claim 12, wherein the tubular reactor is temperature controlled to about 75° C. to about 95° C.

* * * * *